United States Patent [19]
Zarchy

[11] Patent Number: 4,778,944
[45] Date of Patent: Oct. 18, 1988

[54] CATALYTIC ISOMERIZATION OF SULFUR-CONTAINING FEEDSTOCKS

[75] Inventor: Andrew S. Zarchy, Amawalk, N.Y.

[73] Assignee: Union Carbide Corporation, Danbury, Conn.

[21] Appl. No.: 917,654

[22] Filed: Oct. 10, 1986

[51] Int. Cl.$^4$ .............................................. C07C 5/13
[52] U.S. Cl. .................................... 585/739; 585/751
[58] Field of Search ................................ 585/739, 751

[56] References Cited

U.S. PATENT DOCUMENTS 3,925,503  12/1975  Parthasarathy ..................... 585/751

OTHER PUBLICATIONS

Mitsche et al., "Sulfur as a Tool in Catalysis", *Presented Before Div. of Petrol. Chem.*, ACS Los Angeles Meeting Mar. 31–Apr. 5, 1974.
Pfefferle, "The Reaction Chemistry of Catalytic Reforming I. The Rule of Sulfur", Presented Before Div. of Petrol. Chem, ACS Houston Meeting, Feb. 22–27, 1970.
Cheap and Simple Straight Run Naphtha Isomerization by Arthur J. Suchanek, Presented at the 1985 NPRA Annual Meeting, Mar. 24–26, 1985, San Antonio, Texas.
Conversion of a NGL Fractionator Complex to Natural Gasoline Fractionation and N-Pentane Isomerization by Eugene K. O'Gorman Presented at the Gas Processors Assoc., 6th Annual Convention, Mar. 10–12, 1986, San Antonio, TX.

*Primary Examiner*—Curtis R. Davis
*Attorney, Agent, or Firm*—E. Lieberstein

[57] ABSTRACT

Catalytic isomerization of paraffinic feedstocks containing at least about 2 ppm by weight sulfur is effected using an isomerization catalyst comprising a hydrogenation/dehydrogenation catalyst supported on molecular sieve without undue loss of catalytic activity or selectivity by maintaining the water content of the feedstock below about 5 ppm by weight water.

5 Claims, 1 Drawing Sheet

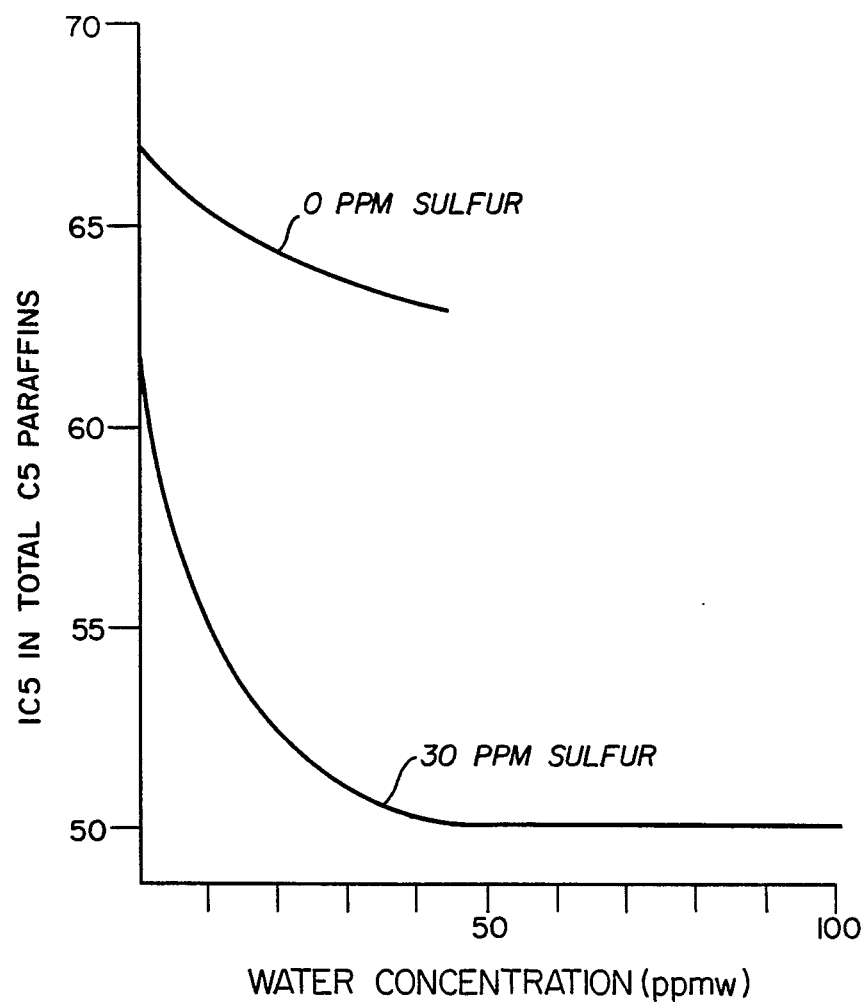

CATALYTIC ISOMERIZATION OF SULFUR-CONTAINING FEEDSTOCKS

This invention relates to the isomerization of paraffinic hydrocarbon feedstocks containing sulfur or sulfur compounds.

Catalytic processes for the isomerization of feedstocks to upgrade octane value are well known. In essence, these processes involve contact of a paraffin containing feedstock with an isomerization catalyst at elevated temperature and pressure in the presence of molecular hydrogen. The catalysts used for isomerization include supported platinum group metal catalysts, e.g., platinum supported on mordenite. These processes have found wide spread use in refining operations to provide enhanced octane rating petroleum products.

Particularly in view of the phase out of tetraethyl lead as an octane enhancing additive, the demand has intensified for processes to increase the octane yield of a hydrocarbon feedstock. Processes such as catalytic isomerization have therefore been considered for up grading a wide variety of hydrocarbon feedstocks in various types of refineries. Such considerations include not only the efficacy of the process but also its costs to install and operate. These costs also include any peripheral equipment necessary to pretreat the feedstock.

Catalytic isomerization is recognized as having sensitivity to elemental sulfur and sulfur compounds (herein referred to as sulfur) and water. For example, in *Hydrocarbon Processing*, September, 1982, the Hysomer process developed by Shell Interationale Research Mij. B.V., is discussed. The process is stated to use a dual function catalyst consisting of a noble metal on a zeolite base and use isomerization conditions including a temperature of 450° to 550° F., a pressure of 200 to 500 psig, a space velocity of 1 to 3 reciprocal hours, and a hydrogen to hydrocarbon mole ratio of 1 to 4. The description further states:

"Feedstock specifications are not stringent. Optimum performance will be obtained with hydrotreated $C_5/C_6$ feedstocks with up to 10 ppm wt sulfur and 30 ppm wt water. However, feedstocks containing up to 100 ppm wt sulfur, water of saturation, a few percent $C_7$s and aromatics, or 15 percent naphthenes can be processed."

Sulfur and water can be provided in the hydrocarbon feedstock as well as other components introduced into the isomerization reaction system. For instance, hydrogen is added to the isomerization system to maintain a desired hydrogen partial pressure. This hydrogen may contain water and/or sulfur and is frequently a significant source of water.

Hydrotreaters are very effective in the removal of sulfur and often reduce the sulfur content of feedstocks to less than about 0.1 ppm by weight. However, not all refineries have hydrotreaters available to reduce the sulfur content of the feedstock to a catalytic isomerization unit, and to install and operate a hydrotreater for feedstocks to an isomerization unit may entail sufficient costs that catalytic isomerization has limited economic attractiveness. Generally, without a hydrotreated, or desulfurized, feedstock, the isomerization catalyst loses activity. The loss of activity often does not stabilize, that is, during the period of operation, the catalyst continues to lose activity. Thus, the useful catalyst life may be too short for an economically viable process.

Accordingly, isomerization processes are sought which enable the processing of sulfur-containing feedstocks with minimal activity loss, catalyst activity stabilization and nominal pretreatment, both in terms of installation and operation.

In accordance with this invention, catalytic isomerization processes are provided that enable the processing of hydrocarbon feedstocks containing at least about 1, often at least about 10, ppm by weight sulfur, yet do not result in undue catalyst activity loss or instability. In the processes of this invention, the water concentration in the feed to the isomerization reactor is maintained no greater than about 5 ppm by weight of water sufficient to retain acceptable catalyst activity and stability. Preferably, the water content of the feed to the isomerization reactor is less than about 3, most preferably 0 to about 2, ppm by weight. With higher concentrations of sulfur, the concentration of water should be lower for better retention of catalyst activity and stability FIG. 1 graphically depicts the effect of water content on initial isomerization performance of a platinum on mordenite catalyst for two feedstocks, one containing no sulfur and the other, 30 ppm by weight sulfur. While in respect of the sulfur free feedstock, water does have some catalyst deactivating activity, the loss of catalyst activity for each incremental increase in water content is much greater with sulfur containing feedstocks. In essence, water appears to make the catalyst more sensitive to sulfur.

FIG. 1 only reports the initial catalyst activity. The effect of water can also be to unstabilize isomerization catalysts. Thus, even if the initial catalyst activity is acceptable, the rate of deterioration of the catalyst may be unacceptable.

Typical feedstocks for isomerization contain water. Even with up stream distillation, the water content of the feedstock may be 10 or 35 ppm by weight or more, and the hydrogen supplied to the isomerization reactor may contain water as well. Thus, in an aspect of the processes of this invention, the feed to the isomerization reactor is dried. Drying may be accomplished by any suitable means including cryogenics, super fractionation, adsorbents and the like; however, from the standpoint of convenience, adsorbents for water such as molecular sieve adsorbents and solid desiccants, e.g., calcium sulfate and silica gel, are often useful. Molecular sieve driers are readily available and are effective and therefore are often preferred. The molecular sieve generally used in the driers is a 3A or 4A molecular sieve. Other similar pore size sieving agents may also find applicability.

The hydrocarbon feedstock for the isomerization usually contains normal and non-normal hydrocarbons. Most frequently, the feedstock is composed principally of the various isomeric forms of saturated hydrocarbons having 5 and 6 carbon atoms.

Suitable feedstocks are typically obtained by refinery distillation operations, and may contain small amounts of $C_7$ and even higher hydrocarbons, but these are typically present, if at all, at below about 2 mole percent. The feedstock may also contain hydrocarbons having 4 and fewer carbon atoms, but generally these are present in amounts less than about 7, most frequently less than about 2, mole percent. Olefinic hydrocarbons are advantageously less than about 4, most frequently less than 0.5, e.g., 0.01 to 0.5, mole percent in the feedstock. Aromatic and cyclo-paraffinic molecules have a relatively high octane number. Since aromatics typically hydrogenate in the reactor to lower octane value components, it is often desired to limit their concentration in the feed to the isomerization reactor, e.g., less than about 5, preferably less than about 2, mole percent. Cycloparaffinic molecules can also be present and may vary over a wide range without undue adverse effect, e.g., up to 50 mole percent or more.

The paraffinic $C_5$ and $C_6$ hydrocarbons typically comprise at least about 60, and more typically at least about 85, mole percent of the feedstock. Preferably, the feedstock will comprise at least about 30, and preferably at least about 40 mole percent, and sometimes up to about 90 or 95 mole percent of a combination of n-pentane and n-hexane.

Hydrocarbon feedstocks that contain sulfur usually have the sulfur in the form of a number of compounds including at least one of mercaptans (e.g., propylmercaptan, butylmercaptan and isobutylmercaptan), sulfides (e.g., dimethyl sulfide, diethyl sulfide and methyl ethyl sulfide), hydrogen sulfide, disulfides (e.g., methyl disulfide and ethyl disulfide) and thiophene.

The isomerization is conducted in the presence of an isomerization catalyst which is a molecular sieve-based catalyst which exhibits selective and substantial isomerization activity under the operating conditions of the isomerization zone. As a general class, such catalysts comprise crystalline molecular sieves having an apparent pore diameter large enough to adsorb neopentane. Frequently, the molecular sieves are zeolitic and have a silica to alumina molar ratio of greater than about 3; less than 60, preferably about 15 to 30, equivalent percent alkali metal cations and having those $AlO_4$-tetrahydra associated with any alkali metal cations either not associated with any metal cation, or associated with a divalent or other polyvalent metal cation. Usually the molecular sieve is a mordenite molecular sieve, which is essentially in the acid form or is converted to the acid form. Suitable mordenite starting materials include the M-5 tradename sodium mordenite and the M-8 tradename acid form mordenite, available from Union Carbide Corporation, Danbury, Conn., U.S.A.

The catalyst is preferably combined with a hydrogenation/dehydrogenation catalyst component, preferably a noble metal of Group VIII of the periodic classification of the elements, especially at least one of platinum and palladium. The hydrogenation/dehydrogenation component is often about 0.1 to 1 weight percent.

The catalyst composition can be used alone or it can be combined with a porous inorganic oxide diluent as a binder material. The hydrogenation catalyst component can be carried either on the molecular sieve component and/or on the binder. It is preferred that the diluent not exhibit an untoward catalytic activity. Diluents include one or more of alumina, silica, zirconia, titania, and clays such as kaolin, attapulgite, sepiolite, polygarskite, bentonite, montmorillonite, and the like. Often the catalyst is in a shaped form, including beads, pellets and the like. Pellets of about 1 millimeter to about 4 millimeters in diameter are frequently used.

Suitable catalysts for isomerization reactions are disclosed in detail in U.S. Pat. Nos. 3,236,761; 3,236,762; 3,442,794; 3,836,597; and 3,842,114, herein incorporated by reference.

Depending on the particular catalyst composition employed, the isomerization conditions include a temperature within the range of 200° to 390° C., preferably, about 220° to 270° C. The pressure within the isomerization reactor is often within the range of about 175 to 600 psia, desirably from about 200 to 500, preferably about 250 to 400, psia. The weight-hourly space velocity of hydrocarbons is usually from about 0.5 to 5, say, about 1 to 3, reciprocal hours based on the weight of catalyst. The isomerization reaction zone is maintained under a hydrogen partial pressure sufficient to prevent coking of the isomerization catalyst at the conditions maintained in the reactor. Typically, the hydrogen partial pressure will be within the range of about 100 to 500. preferably from about 130 to 250, psia with the hydrogen, on average, comprising from about 40 to 80, preferably from about 60 to 80, and most preferably from about 65 to 80, mole percent of the gases contained in the reactor. Hydrogen may be obtained from any convenient source, and, in many refining operations, it is derived from off-gases from other processing units.

In the embodiments of this invention in which the feed to the reactor is dried, several options exist. For instance, all or a part of the feed to the isomerization reactor may be dried to provide the desired low water content. Often the hydrocarbon feedstock may be dried, and, in most instances, both the hydrogen feedstock and make-up hydrogen to be passed to the isomerization reactor are dried due to the water content that may be associated with the hydrogen.

When, for example, molecular sieve is used for drying, thermal swing adsorber are often attractive. The drying operation can be conducted in any suitable manner. Usually the adsorption is effected at temperatures of about ambient to 70° C., say, about 25° C. to 50° C., and the adsorber volume is sufficient to provide a substantial cycle time, e.g, at least about 2 hours, say, about 6 to 20 hours. The effluent from the drier preferably contains less than about 2, often less than about 1, ppm by weight of water. Regeneration is conducted at elevated temperatures, e.g., at least about 100° C., say, at least about 150° C. and often about 150° C. to 300° C. A dry sweep gas is typically used to facilitate the regeneration. The sweep gas should be relatively dry, and product from another adsorber, nitrogen or other suitable gas may be used. Drying can also be effected by pressure swing adsorption techniques.

The product from the isomerization reactor may be directly utilized for octane upgrading purposes or it may be passed to a separation zone to recover the nonnormal hydrocarbons from the normal hydrocarbons. The normal hydrocarbons can then be recycled to the isomerization reactor for further reaction. One such separation operation involves the use of a molecular sieve adsorbent having an apparent pore diameter of between about 4 and 6 Angstroms. This process is described in, for instance, U.S. Pat. Nos. 3,770,589 and 3,770,621, both herein incorporated by reference.

The following examples are provided to further illustrate the invention but are not in limitation of the invention. All parts and percentages of gases and liquids are by volume and solids, unless otherwise indicated, are by weight.

EXAMPLE 1

In this example a platinum on mordenite isomerization catalyst is used. The catalyst contains about 0.32 to 0.33 weight percent platinum supported on an acid form mordenite (M-8) obtained from the Union Carbide Corporation, Danbury, Conn., U.S.A., and is in the shape of a pellet having about a one-sixteenth inch diameter. Approximately 100 grams of catalyst are placed in a tubular reactor having about a two inch diameter. The length of the reactor is about three feet (although the catalyst bed is only a small section of the overall length of the reactor). Above the catalyst bed are approximately 100 grams of quartz chips (about ¼ inch diameter and 1/16 inch in thickness). The reactor is enclosed in a furnace suitable to control the temperature of the bed.

In operation, the hydrocarbon feed is admixed with hydrogen and passed to the top of the reactor where the hydrocarbon is vaporized. Reaction product is withdrawn from the bottom of the reactor, cooled to ambient temperature (about 20° to 25° C.) and flashed to obtain a liquid sample and a gaseous off product. The volumes of the gaseous off product and liquid produced over a period of time are measured and the gas and liquid are analyzed by gas chromatography to ascertain their compositions. The analysis determines the weight percent isopentane for the total $C_5$ content of the products. The higher that this percentage is, the greater the activity of the catalyst.

In the runs set forth below, the hydrocarbon feed is a light commercial feedstock containing about 0.1 weight percent of $C_4$ and lowers, 3.6 weight percent of isopentane, 92.0 weight percent n-pentane, 3.8 weight percent other pentane isomers and 0.5 weight percent $C_6$ and highers. The feed contains 25 ppm by weight sulfur and 18 ppm by weight water. The hydrogen is analytical, bottled hydrogen. The runs are conducted at a total pressure of about 300 psig, a weight hourly space velocity (based on the hydrocarbon feed) of 1.65 reciprocal hours based on the weight of catalyst, and a hydrogen to hydrocarbon mole ratio of about 1.0. In each run, the temperature of the reactor is changed from 480° F., 500° F., 520° F. and 540° F. with product samples being taken at each temperature.

Run A is conducted as set forth above and Run B is conducted in substantially the same manner except that the hydrocarbon feed (liquid) is passed through a column containing about 100 grams of 4A molecular sieve that reduces the water content of the feed to about 0.1 ppm by weight. Table A summarizes the results.

TABLE A

| Reactor Temperature, degrees C. | %, iC$_5$ in Total C$_5$ s | |
|---|---|---|
| | Run A | Run B |
| 480 | 30 | 35 |
| 500 | 40 | 50 |
| 520 | 53 | 62 |
| 540 | 59 | 67 |

EXAMPLE II

A pilot plant substantially the same as that set forth in Example I is used for the isomerization of a heavy commercial feedstock containing about 19.9 weight percent n-pentane, 9.8 weight percent isopentane, 2.5 weight percent cyclopentane, 2.4 weight percent other C$_5$s, 23.1 weight percent n-hexane, 11.3 weight percent methyl cyclopentane, 15.9 weight percent 2 methylpentane, 9.7 weight percent 3 methylpentane, 3.6 weight percent benzene, 1.5 weight percent cyclohexane, and 0.1 weight percent $C_7$ and highers. The feedstock contains about 180 ppm by weight sulfur (100 ppm by weight mercaptans, 72 ppm by weight sulfides, 7 ppm by weight thiophene, and 1 ppm hydrogen sulfide), and 35 ppm by weight water. The hydrogen is building services hydrogen. The samples are collected over about a one hour period. The isomerization catalyst is subtantially the same as that described in Example I. The reactor pressure is about 250 psig, the space velocity is about 1.0 and the hydrogen to hydrocarbon mole ratio is about 3. The runs are conducted at a reaction temperature of about 525° F.

As in Example I, Run A is without drying and Run B is with drying the feed to below about 0.1 ppm by weight H$_2$O using a drier of the type described in Example I. The results are summarized in Table B which reports the change in catalyst activity over a four day operating period.

TABLE B

| | Weight Percent iC$_5$ in total C$_5$ | |
|---|---|---|
| Days on Line | Run A | Run B |
| 1 | 56 | 64 |
| 2 | 54 | 58 |
| 3 | 52 | 57 |
| 4 | 50 | 58 |

In summary, Examples I and II illustrate that the delecterious effect of sulfur on isomerization catalysts can be materially reduced by the use of low water-content feeds.

It is claimed:

1. A process for upgrading the octane of an isomerable hydrocarbon feedstock comprising at least about 60 mole % praaffinic C$_5$ and C$_6$ hydrocarbons and at least 1 ppm sulfur and at least 5 ppm water in which the feedstock is combined with H$_2$ and passed through an isomerization reactor containing an isomerization catalyst comprising noble metal supported on molecular sieve under isomerization conditions, the improvement comprising; drying the feedstock prior to contact with the isomerization catalyst until the concentration of water in the feedstock is reduced to a level below at least 3 ppm by weight whereby the isomerization catalyst becomes substantially sulfur tolerant.

2. The process of claim 1 wherein the isomerization catalyst comprises at least one of platinum and palladium on a molecular sieve.

3. The process of claim 2 wherein the sulfur content of the feedstock is at least about 10 ppm by weight.

4. The process of claim 2 wherein the drying is effected by molecular sieve adsorbent.

5. The process of claim 1 wherein the catalyst comprises at least one of platinum and palladium on mordenite.

* * * * *

UNITED STATES PATENT AND TRADEMARK OFFICE
CERTIFICATE OF CORRECTION

PATENT NO. : 4,778,944
DATED : 10/18/88
INVENTOR(S) : Andrew S. Zarchy

It is certified that error appears in the above-identified patent and that said Letters Patent is hereby corrected as shown below:

at col. 1, line 16 wide spread should be widespread.

at col. 2, line 19 stability should have a period after it.

at col. 3, line 39 tradename should be trade name.

at col. 4, line 28 adsorber should be adsorbers.

at col. 5, line 23 lowers should be lower.

at col. 6, line 31 delecterious should be deleterious.

at col. 6, line 37 praaffinic should be paraffinic.

at col. 6, line 44 there should be no ; next to comprising.

Signed and Sealed this

Thirteenth Day of June, 1989

Attest:

DONALD J. QUIGG

*Attesting Officer*  *Commissioner of Patents and Trademarks*